(12) United States Patent
Webber

(10) Patent No.: US 8,618,025 B2
(45) Date of Patent: Dec. 31, 2013

(54) COMPOSITION AND METHOD FOR REDUCING HYDRATE AGGLOMERATION

(75) Inventor: Peter A. Webber, Sugar Land, TX (US)

(73) Assignee: Nalco Company, Naperville, IL (US)

( * ) Notice: Subject to any disclaimer, the term of this patent is extended or adjusted under 35 U.S.C. 154(b) by 0 days.

(21) Appl. No.: 12/970,280

(22) Filed: Dec. 16, 2010

(65) Prior Publication Data

US 2012/0157351 A1  Jun. 21, 2012

(51) Int. Cl.
C07C 229/26 (2006.01)
C09K 8/52 (2006.01)

(52) U.S. Cl.
USPC ............. 507/240; 507/90; 507/241; 507/244; 507/265; 507/267; 560/169; 166/304

(58) Field of Classification Search
USPC ..................... 507/90, 203, 239, 240, 241, 267
See application file for complete search history.

(56) References Cited

U.S. PATENT DOCUMENTS

| | | | | |
|---|---|---|---|---|
| 3,317,556 A * | 5/1967 | Rose et al. | ................. | 548/351.1 |
| 3,894,962 A * | 7/1975 | Allain et al. | ................... | 502/159 |
| 4,081,402 A | 3/1978 | Levy et al. | | |
| 4,652,623 A * | 3/1987 | Chen et al. | ..................... | 526/287 |
| 4,673,716 A | 6/1987 | Siano et al. | | |
| 4,980,378 A | 12/1990 | Wong et al. | | |
| 5,981,816 A | 11/1999 | Sinquin et al. | | |
| 6,177,497 B1 | 1/2001 | Klug et al. | | |
| 6,194,622 B1 | 2/2001 | Peiffer et al. | | |
| 6,319,971 B1 | 11/2001 | Kelland et al. | | |
| 6,398,967 B2 | 6/2002 | Sparapany et al. | | |
| 6,451,891 B1 | 9/2002 | Thieu et al. | | |
| 6,559,233 B2 | 5/2003 | Bavouzet et al. | | |
| 6,702,946 B1 | 3/2004 | Huang et al. | | |
| 6,905,605 B2 | 6/2005 | Klomp | | |
| 7,073,588 B2 * | 7/2006 | Cassidy et al. | ................. | 166/307 |
| 7,214,814 B2 * | 5/2007 | Dahlmann et al. | ............ | 560/155 |
| 7,253,138 B2 | 8/2007 | Dahlmann et al. | | |
| 7,311,144 B2 | 12/2007 | Conrad | | |
| 7,408,004 B2 | 8/2008 | Struck et al. | | |
| 7,452,848 B2 | 11/2008 | Meier et al. | | |
| 7,550,339 B2 | 6/2009 | Forbes | | |
| 2003/0130454 A1 | 7/2003 | Seya et al. | | |
| 2004/0009880 A1* | 1/2004 | Fu | ................................ | 507/200 |
| 2004/0094301 A1* | 5/2004 | Hughes et al. | ............. | 166/308.2 |
| 2004/0102330 A1* | 5/2004 | Zhou et al. | ..................... | 507/100 |
| 2004/0164278 A1 | 8/2004 | Dahlmann et al. | | |
| 2005/0085396 A1 | 4/2005 | Panchalingam et al. | | |
| 2005/0101495 A1 | 5/2005 | Dahlmann et al. | | |
| 2006/0094913 A1 | 5/2006 | Spratt | | |
| 2006/0205603 A1 | 9/2006 | Colle et al. | | |
| 2007/0173672 A1 | 7/2007 | Dahlmann et al. | | |
| 2008/0113890 A1 | 5/2008 | Moreton et al. | | |
| 2008/0177103 A1 | 7/2008 | Leinweber et al. | | |
| 2010/0087338 A1* | 4/2010 | Acosta | ............. | 507/90 |
| 2010/0087339 A1* | 4/2010 | Acosta | ............. | 507/90 |
| 2010/0099807 A1 | 4/2010 | Carlise et al. | | |
| 2010/0099814 A1 | 4/2010 | Conrad et al. | | |
| 2010/0222239 A1 | 9/2010 | Acosta et al. | | |

FOREIGN PATENT DOCUMENTS

| | | | |
|---|---|---|---|
| GB | 962242 A1 * | 6/1961 | |
| GB | 960622 A1 * | 6/1964 | |
| GB | 962242 A * | 7/1964 | |
| JP | 58-185671 A | 10/1983 | |
| JP | 01038080 A | 2/1989 | |
| WO | 0240433 | 5/2002 | |
| WO | 2004032824 | 4/2004 | |
| WO | 2004041884 | 5/2004 | |
| WO | 2004111161 A1 | 12/2004 | |
| WO | 2006051265 | 5/2006 | |
| WO | 2008089262 | 7/2008 | |

OTHER PUBLICATIONS

Sharma et al., "Green and mild protocol for hetero-Michael addition of sulfur and nitrogen nucleophiles in ionic liquid", Journal of Molecular Catalysis, A: Chemical, 277, pp. 21-220, 2007.
V. Fedi et al., Inseration of an Aspartic Acid Moiety into Cyclic Pseudopeptides: Synthesis and Biological Characterization of Potent Antagonists for the Human Tachykinin NK-2 Receptor, Journal of Medicinal Chemistry, vol. 47, pp. 6935-6947, 2004.
Billmeyer, F., Textbook of Polymer Science, John Wiley & Sons, Inc., 3rd edition, p. 5, 1984.
Yadav, J.S. et al., "Synthesis", No. 22, pp. 3447-3450, 2007.
Graham, Promoter Action in Reactions of Oxidation Concomitant with the Catalytic Decomposition of Hydrogen Peroxide. I. The Oxidation of Hydrazine. The Journal of the American Chemical Society, 1930, vol. 52, pp. 3035-3045.

\* cited by examiner

*Primary Examiner* — John J Figueroa
(74) *Attorney, Agent, or Firm* — Edward O. Yonter; Andrew D. Sorensen

(57) ABSTRACT

Disclosed and claimed is a composition and method of inhibiting the formation of hydrate agglomerates in a fluid comprising water, gas, and optionally liquid hydrocarbon comprising adding to the fluid an effective anti-agglomerant amount of the following formula and optionally salts thereof:

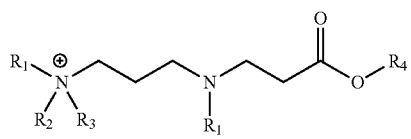

wherein each $R_1$ is independently absent, $C_1$-$C_{10}$ alkyl, benzyl, or H; wherein $R_2$ is $C_1$-$C_{10}$ alkyl; wherein $R_3$ $C_1$-$C_{10}$ alkyl; and wherein $R_4$ is $C_4$-$C_{22}$ alkyl or alkenyl.

20 Claims, No Drawings

COMPOSITION AND METHOD FOR REDUCING HYDRATE AGGLOMERATION

TECHNICAL FIELD OF THE INVENTION

This invention relates generally to reducing or inhibiting the formation and growth of hydrate particles in fluids containing hydrocarbon gas and water. More specifically, the invention relates to reducing or inhibiting such formation in the production and transport of natural gas, petroleum gas, or other gases. The invention has particular relevance to treating such systems with beta-amino ester surfactants as anti-agglomerates to reduce or inhibit the formation of gas hydrates.

BACKGROUND OF THE INVENTION

Since Hammerschmidt discovered in 1934 that gas hydrates would block gas pipelines, research for the prevention of hydrate formation and agglomeration has become an important matter. Gas hydrates can be easily formed during the transportation of oil and gas in pipelines when the appropriate conditions are present. Water content, low temperatures, and elevated pressure are required for the formation of gas hydrates. The formation of gas hydrates often result on lost oil production, pipeline damage, and safety hazards to field workers. Modern oil and gas technologies commonly operate under severe conditions during the course of oil recovery and production; for instance, high pumping speed, high pressure in the pipelines, extended length of pipelines, and low temperature of the oil and gas flowing through the pipelines. These conditions are particularly favorable for the formation of gas hydrates, which can be particularly hazardous for oil productions offshore or for locations with cold climates.

Gas hydrates are ice-like solids that are formed from small nonpolar molecules and water at lower temperatures and at increased pressures. Under these conditions, the water molecules can form cage-like structures around these small nonpolar molecules (typically dissolved gases such as carbon dioxide, hydrogen sulfide, methane, ethane, propane, butane and iso-butane), creating a type of host-guest interaction also known as a clathrate or clathrate hydrate. The specific architecture of this cage structure can be one of several types (called type 1, type 2, type H), depending on the identity of the guest molecules. However, once formed, these crystalline cage structures tend to settle out from the solution and accumulate into large solid masses that can travel by oil and gas transporting pipelines, and potentially block or damage the pipelines and/or related equipment. The damage resulting from a blockage can be very costly from an equipment repair standpoint, as well as from the loss of production, and finally the resultant environmental impact.

The industry uses a number of methods to prevent such blockages such as thermodynamic hydrate inhibitors (THI), anti-agglomerates (AA), and kinetic hydrate inhibitors (KHI). The amount of chemical needed to prevent blockages varies widely depending upon the type of inhibitor that is employed. Thermodynamic hydrate inhibitors are substances that can reduce the temperature at which the hydrates form at a given pressure and water content and are typically used at very high concentrations (regularly dosed as high as 50% based on water content—glycol is often used in amounts as high as 100% of the weight of the produced water). Therefore, there is a substantial cost associated with the transportation and storage of large quantities of these solvents.

A more cost-effective alternative is the use of LDHIs, as they generally require less that 2% dose to inhibit the nucleation or growth of gas hydrates. There are two general types of LDHIs, kinetic hydrate inhibitors (KHIs) and anti-agglomerates (AAs), which are both typically used at much lower concentrations (0.3-0.5% active concentration). KHIs work by delaying the growth of gas hydrate crystals and as anti-nucleators. AAs allow the hydrates to form but they prevent them from agglomerating and subsequent accumulation into larger masses capable of causing plugs. An AA enables gas hydrates to form but in the shape of fluid slurry dispersed in the liquid hydrocarbon phase. In general, the water cut should be below 50% otherwise the slurry become too viscous to transport.

There is therefore an ongoing need for new and effective methods of inhibiting the formation of hydrate agglomerates, particularly those that are capable of operating under higher water-cuts.

BRIEF SUMMARY OF THE INVENTION

Accordingly, this invention pertains to anti-agglomerant compositions as well as methods for inhibiting the formation of hydrate agglomerates in an aqueous medium comprising water, gas, and optionally liquid hydrocarbon.

In one aspect, the present invention relates to the synthesis and use of beta-amino ester surfactants as anti-agglomerates. These surfactants comprise 3-(dialkylamino)-1-propylamine as the hydrophilic portion of the molecule and a fatty alkyl group as the hydrophobic portion of the molecule. Such anti-agglomerates provide for a composition comprising the following formula and optionally salts thereof.

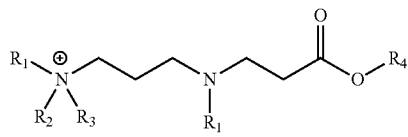

Each $R_1$ is independently $C_1$-$C_{10}$ alkyl, benzyl, or H. In an embodiment, at least one $R_1$ is absent. $R_2$ and $R_3$ are independently $C_1$-$C_{10}$ alkyl. $R_4$ is $C_4$-$C_{22}$ alkyl or alkenyl.

In an embodiment, a counterion is present when $R_1$ is present on a quaternary or cationic nitrogen.

In another aspect, the present invention provides for a method of inhibiting the formation of hydrate agglomerates in an aqueous medium comprising water, gas, and optionally liquid hydrocarbon comprising adding to the aqueous medium an effective anti-agglomerating amount of a composition comprising the above formula and optionally salts thereof.

In an embodiment, a counterion is present when $R_1$ is present on a quaternary or cationic nitrogen.

It is an advantage of the invention to provide anti-agglomerate compositions useful for the prevention of hydrate plugs in oil production pipes.

It is another advantage of the invention to provide anti-agglomerate compositions that do not negatively affect the overboard water quality.

It is a further advantage of the invention to provide anti-agglomerate compositions that are capable to be delivered in subsea umbilical lines.

The foregoing has outlined rather broadly the features and technical advantages of the present invention in order that the detailed description of the invention that follows may be better understood. Additional features and advantages of the invention will be described hereinafter that form the subject of the claims of the invention. It should be appreciated by those skilled in the art that the conception and the specific embodiments disclosed may be readily utilized as a basis for modifying or designing other embodiments for carrying out the same purposes of the present invention. It should also be realized by those skilled in the art that such equivalent embodiments do not depart from the spirit and scope of the invention as set forth in the appended claims.

DETAILED DESCRIPTION

The compositions of the invention comprise a generic formula and optionally salts thereof as given below.

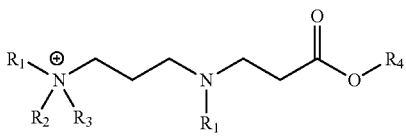

In one embodiment, at least one $R_1$ is absent. In another embodiment, each $R_1$ is independently $C_1$-$C_{10}$ alkyl, benzyl, or H. $R_2$ and $R_3$ are independently $C_1$-$C_{10}$ alkyl. $R_4$ is $C_4$-$C_{22}$ alkyl or alkenyl. In an embodiment, a counterion is present when $R_1$ is present on a quaternary or cationic nitrogen. The presence of $R_1$, although not required, generally improves the properties of the composition in terms of anti-agglomeration and water quality. Moreover, it is thought that the presence of the ester group in the generic structure may allow for improved biodegradation profiles.

"Alkenyl" means a monovalent group derived from a straight, branched, or cyclic hydrocarbon containing at least one carbon-carbon double bond by the removal of a single hydrogen atom from each of two adjacent carbon atoms of an alkyl group. Representative alkenyl groups include, for example, ethenyl, propenyl, butenyl, 1-methyl-2-buten-1-yl, and the like.

"Alkyl" refers to a monovalent group derived by the removal of a single hydrogen atom from a straight or branched chain or cyclic saturated or unsaturated hydrocarbon. Representative alkyl groups include methyl, ethyl, propyl, butyl, pentyl, hexyl, heptyl, octyl, nonyl, and decyl.

"Counterion" refers to a halide selected from fluoride, chloride, bromide, iodide, or carboxylate selected from reaction with mineral acid, acrylic acid, acetic acid, methacrylic acid, glycolic acid, thioglycolic acid, propionic acid, butyric acid, the like, and any combination thereof.

In one embodiment, the composition comprises the following formula and optionally salts thereof:

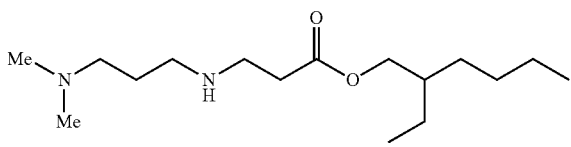 [SMILES: CCCCC(CC)COC(=O)CCNCCCN(C)C]

In another embodiment, the composition comprises the following formula and optionally salts thereof:

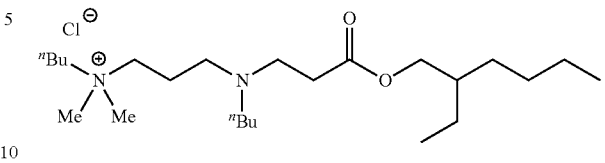

In another embodiment, the composition comprises the following formula and optionally salts thereof:

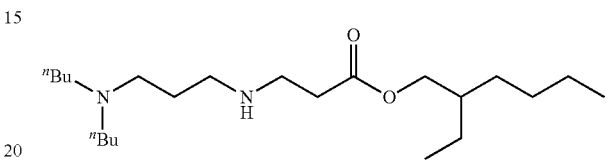

In another embodiment, the composition comprises the following formula and optionally salts thereof:

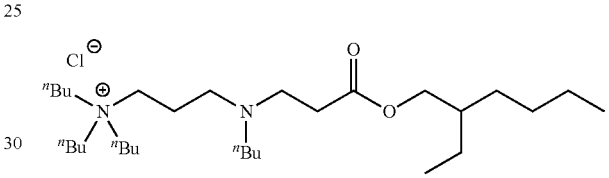

In another embodiment, the composition comprises the following formula and optionally salts thereof:

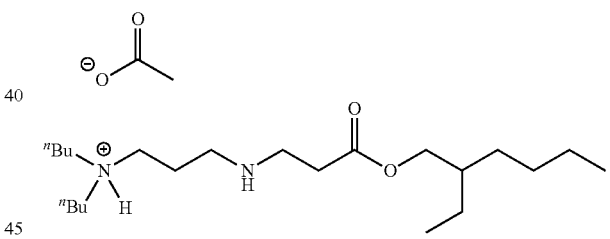

Various synthesis methodologies, which can be appreciated by one of ordinary skill in the art, can be utilized to make the claimed compositions.

The compositions of this invention can contain one or more additional chemistries. Various formulations can be appreciated by one of ordinary skill in the art and can be made without undue experimentation.

In one embodiment, the composition further comprises at least one additional hydrate inhibitor. Exemplary hydrate inhibitors are disclosed in U.S. patent application Ser. Nos. 12/253,504, "Method of Controlling Gas Hydrates in Fluid Systems," filed Oct. 17, 2008, 12/253,529, "Method of Controlling Gas Hydrates in Fluid Systems," filed Oct. 17, 2008, 12/400,428, "Compositions and Methods for Inhibiting the Agglomeration of Hydrates in a Process," filed Mar. 9, 2009, all currently pending.

In another embodiment, the composition further comprises one or more thermodynamic hydrate inhibitors, one or more kinetic hydrate inhibitors, one or more anti-agglomerants, or a combination thereof.

In another embodiment, the composition further comprises one or more asphaltene inhibitors, paraffin inhibitors, corrosion inhibitors, scale inhibitors, emulsifiers, water clarifiers, dispersants, emulsion breakers, or a combination thereof.

In another embodiment, the composition further comprises one or more polar or nonpolar solvents or a mixture thereof.

In another embodiment, the composition further comprises one or more solvents selected from isopropanol, methanol, ethanol, 2-ethylhexanol, heavy aromatic naptha, toluene, ethylene glycol, ethylene glycol monobutyl ether (EGMBE), diethylene glycol monoethyl ether, xylene, or a combination thereof.

The composition is introduced into the fluid by any means suitable for ensuring dispersal of the inhibitor through the fluid being treated. Typically the inhibitor is injected using mechanical equipment such as chemical injection pumps, piping tees, injection fittings, and the like. The inhibitor mixture can be injected as prepared or formulated in one or more additional polar or non-polar solvents depending upon the application and requirements.

Representative polar solvents suitable for formulation with the inhibitor composition include water, brine, seawater, alcohols (including straight chain or branched aliphatic such as methanol, ethanol, propanol, isopropanol, butanol, 2-ethylhexanol, hexanol, octanol, decanol, 2-butoxyethanol, etc.), glycols and derivatives (ethylene glycol, 1,2-propylene glycol, 1,3-propylene glycol, ethylene glycol monobutyl ether, etc.), ketones (cyclohexanone, diisobutylketone), N-methylpyrrolidinone (NMP), N,N-dimethylformamide and the like.

Representative of non-polar solvents suitable for formulation with the inhibitor composition include aliphatics such as pentane, hexane, cyclohexane, methylcyclohexane, heptane, decane, dodecane, diesel, and the like; aromatics such as toluene, xylene, heavy aromatic naptha, fatty acid derivatives (acids, esters, amides), and the like.

In embodiments of the invention, the disclosed composition is used in a method of inhibiting the formation of hydrate agglomerates in an aqueous medium comprising water, gas, and optionally liquid hydrocarbon. The method comprises adding to the aqueous medium an effective anti-agglomerant amount of the disclosed composition.

The composition and method of this invention is effective to control gas hydrate formation and plugging in hydrocarbon production and transportation systems. To ensure effective inhibition of hydrates, the inhibitor composition should be injected prior to substantial formation of hydrates. A preferred injection point for petroleum production operations is downhole near the near the surface controlled sub-sea safety valve. This ensures that during a shut-in, the product is able to disperse throughout the area where hydrates will occur. Treatment can also occur at other areas in the flowline, taking into account the density of the injected fluid. If the injection point is well above the hydrate formation depth, then the hydrate inhibitor should be formulated with a solvent with a density high enough that the inhibitor will sink in the flowline to collect at the water/oil interface. Moreover, the treatment can also be used for pipelines or anywhere in the system where there is a potential for hydrate formation.

In embodiments, the composition is applied to an aqueous medium that contains various levels of salinity. In one embodiment, the fluid has a salinity of 1% to 25% weight/weight (w/w) total dissolved solids (TDS). The aqueous medium in which the disclosed compositions and/or formulations are applied can be contained in many different types of apparatuses, especially those that transport an aqueous medium from one point to another point.

In embodiments, the aqueous medium is contained in an oil and gas pipeline. In other embodiments, the aqueous medium is contained in refineries, such as separation vessels, dehydration units, gas lines, and pipelines.

In embodiments, the composition is applied to an aqueous medium that contains various levels of water cut. One of ordinary skill in the art would interpret water cut to mean the % of water in a composition containing an oil and water mixture. In one embodiment, the water cut is from 1 to 80% w/w total dissolved solids.

The compositions of the present disclosure and/or formulations thereof can be applied to an aqueous medium in various ways that would be appreciated by of ordinary skill in the art. One of ordinary skill in the art would appreciate these techniques and the various locations to which the compositions or chemistries can be applied.

In one embodiment, the compositions and/or formulations are pumped into the oil/gas pipeline by using an umbilical line. In a further embodiment, capillary string injection systems can be utilized to deliver the compositions and/or formulations of the invention, in this case anti-agglomerants. U.S. Pat. No. 7,311,144 provides a description of an apparatus and methods relating to capillary injection.

Various dosage amounts of a composition and/or formulation can be applied to the aqueous medium to inhibit the formation of hydrate agglomerates. One of ordinary skill in the art would be able to calculate the amount of anti-agglomerant for a given situation without undue experimentation. Factors that would be considered of importance in such calculations include, for example, content of aqueous medium, percentage water cut, API gravity of hydrocarbon, and test gas composition.

In one embodiment, the dose range for the hydrate inhibitor that is applied to an aqueous medium is between about 0.1% volume to about 3% volume based on water cut. In another embodiment, the dose range is from about 0.25% volume to about 1.5% volume based on water cut.

The methodologies described in the present invention may be utilized with other compositions that are commensurate in scope with this disclosure. Other chemistries used for inhibiting the formation of agglomerants in fluids, which are outside the specific generic formula described above, but are commensurate in scope with the claimed compositions generic formula, may be utilized if the system conditions permit the compositions to inhibit the formation of agglomerants (hydrate agglomerates). This protocol can be achieved without undue experimentation, specifically, for example, the rocking test described below can be utilized in determining whether a chemistry works or not The foregoing may be better understood by reference to the following examples, which are intended for illustrative purposes and are not intended to limit the scope of the invention.

Example 1

This example illustrates an embodiment of the composition of invention. A representative synthetic procedure for 2-ethylhexyl 3-(3-(dimethylamino)propylamino) propanoate is described.

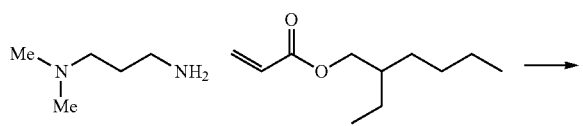

-continued

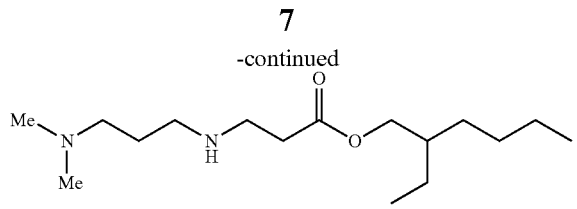

To a 500-mL, 3-neck round bottom flask was added 50.0 g (0.49 . mol) 3-(dimethylamino)-1-propylamine and a magnetic stirbar. The flask was fitted with a thermocouple, reflux condenser, and addition funnel containing 90.2 g (0.49 mol) 2-ethylhexylacrylate. The acrylate was added to the stirring amine in three equal volume shots. Once the addition was complete, the reaction mixture was heated to 100° C. for 5 hours. The final product was a light yellow liquid at ambient temperature. Complete conversion is apparent by the disappearance of the diamine starting material by TLC (1/5CHCl$_3$/MeOH with 0.5% v/v NH$_4$OH).

Example 2

This example illustrates an embodiment of the composition of invention. A representative synthetic procedure for N-(3-(butyl(3-(2-ethylhexyloxy)-3-oxopropyl)amino)propyl)-N,N-dimethylbutan-1-aminium chloride is described.

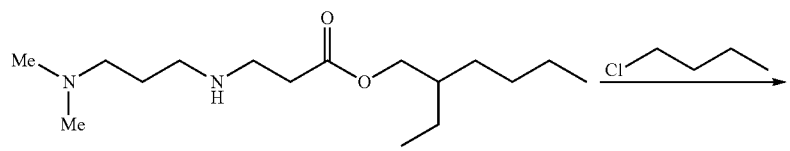

To a 220 mL volume capacity sealed tube was added 25.0 g (87.3 mmol) 2-ethylhexyl 3-(3-(dimethylamino)propylamino)propanoate, 16.2 g (174.6 mmol) 1-chlorobutane, 8.27 g 2-propanol, and a magnetic stir bar. The tube was sealed tightly and heated in a silicone oil bath for 21 hours at 130° C. Complete conversion was apparent by the disappearance of the diamine starting material by TLC (1/5CHCl$_3$/MeOH with 0.5% v/v NH$_4$OH).

Example 3

This example illustrates an embodiment of the composition of invention. A representative synthetic procedure for 2-ethylhexyl 3-(3-(dibutylamino)propylamino)propanoate is described.

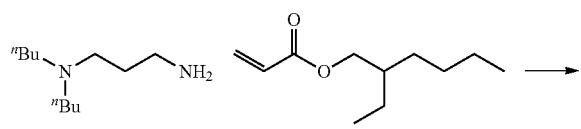

-continued

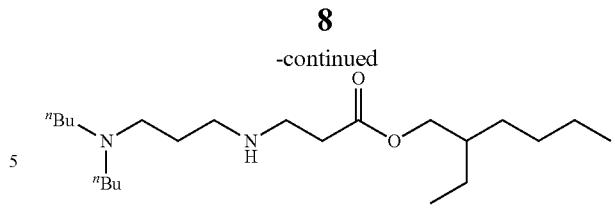

To a 500-mL, 3-neck round bottom flask was added 50.0 g (0.27 . mol) 3-(dibutylamino)-1-propylamine and a magnetic stirbar. The flask was fitted with a thermocouple, reflux condenser, and addition funnel containing 49.4 g (0.27 mol) 2-ethylhexylacrylate. The acrylate was added to the stirring amine in three equal volume shots. Once the addition was complete, the reaction mixture was heated to 100° C. for 5 hours. The final product was a light yellow liquid at ambient temperature. Complete conversion is apparent by the disappearance of the diamine starting material by TLC (1/5CHCl$_3$/MeOH with 0.5% v/v NH$_4$OH).

Example 4

This example illustrates an embodiment of the composition of invention. A representative synthetic procedure for N-butyl-N-(3-(3-(2-ethylhexyloxy)-3-oxopropylamino)propyl)butan-1-aminium acetate is described.

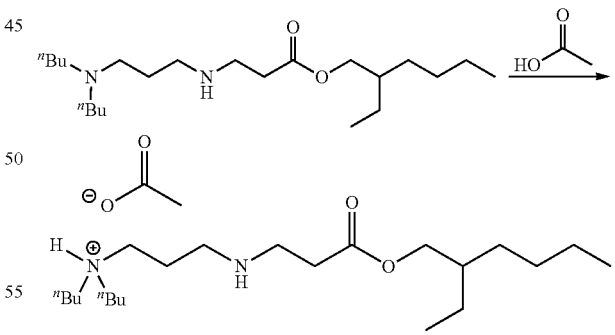

To a 500-mL 3-neck round bottom flask was added 99.4 g 2-ethylhexyl 3-(3-(dibutylamino)propylamino)propanoate and a magnetic stirbar. The flask was fitted with a thermocouple, reflux condenser, and addition funnel containing 16.1 g (0.27 mol) acetic acid. The acetic acid was added at ambient temperature to the slowly over 10 minutes. Once the addition was complete, the reaction mixture was stirred for 2 hours at ambient temperature. The final product was a thick orange liquid at ambient temperature.

Structures of Table 1 are, for example, the quaternization products of the reaction of 1-bromobutane with the adduct formed from the addition of 2-ethylhexylacrylate to (3-dimethylamino)-1-propylamine or the quaternization products of the reaction of 1-chlorobutane with the adduct formed from the addition of commercially available 2-ethylhexylacrylate to (3-dimethylamino)-1-propylamine. All of the quaternary ammonium species are soluble in 2-propanol (IPA), methanol, ethylene glycol (MEG), ethylene glycol monobutyl ether (EGMBE), and combinations thereof. Variable in Structures 1 to 18 of Table 1 refer to the general formula below.

TABLE 1

$$X^{\ominus} \quad R_1 \overset{\oplus}{\underset{R_2 \ R_3}{N}} \diagdown\diagup\diagdown N(R_1) \diagdown\diagup\diagdown C(=O)O\diagup R_4$$

| Structure | $R_1$ | $R_2$ | $R_3$ | $R_4$ | X | Solvent |
|---|---|---|---|---|---|---|
| 1 | $C_4H_9$ | $CH_3$ | $CH_3$ | $C_8H_{17}$ | Cl | IPA/MeOH |
| 2 | $C_4H_9$ | $CH_3$ | $CH_3$ | $C_8H_{17}$ | Cl | IPA/MEG |
| 3 | $C_4H_9$ | $CH_3$ | $CH_3$ | $C_8H_{17}$ | Cl | EGMBE/MEG |
| 4 | $C_4H_9$ | $CH_3$ | $CH_3$ | $C_8H_{17}$ | Br | IPA/MeOH |
| 5 | $C_4H_9$ | $CH_3$ | $CH_3$ | $C_8H_{17}$ | Br | IPA/MEG |
| 6 | $C_4H_9$ | $CH_3$ | $CH_3$ | $C_8H_{17}$ | Br | EGMBE/MEG |
| 7 | $C_6H_{13}$ | $CH_3$ | $CH_3$ | $C_8H_{17}$ | Br | IPA/MeOH |
| 8 | $C_6H_{13}$ | $CH_3$ | $CH_3$ | $C_8H_{17}$ | Br | IPA/MEG |
| 9 | $C_6H_{13}$ | $CH_3$ | $CH_3$ | $C_8H_{17}$ | Br | EGMBE/MEG |
| 10 | $C_4H_9$ | $CH_3$ | $CH_3$ | $C_{12}H_{25}$ | Cl | IPA/MeOH |
| 11 | $C_4H_9$ | $CH_3$ | $CH_3$ | $C_{12}H_{25}$ | Cl | IPA/MEG |
| 12 | $C_4H_9$ | $CH_3$ | $CH_3$ | $C_{12}H_{25}$ | Cl | EGMBE/MEG |
| 13 | H | $C_4H_9$ | $C_4H_9$ | $C_8H_{17}$ | acetate | MeOH |
| 14 | H | $C_4H_9$ | $C_4H_9$ | $C_8H_{17}$ | acetate | IPA |
| 15 | H | $C_4H_9$ | $C_4H_9$ | $C_8H_{17}$ | acetate | EGMBE/MEG |
| 16 | H | $C_4H_9$ | $C_4H_9$ | $C_{12}H_{25}$ | acetate | MeOH |
| 17 | H | $C_4H_9$ | $C_4H_9$ | $C_{12}H_{25}$ | acetate | IPA |
| 18 | H | $C_4H_9$ | $C_4H_9$ | $C_{12}H_{25}$ | acetate | EGMBE/MEG |

Example 4

Certain of structures 1 to 18 were dissolved to 40% w/w for the anti-agglomeration test (Table 2). The rocking cell test is the primary test for assessing the performance of an anti-agglomerate chemistry. Chemistries were evaluated based on their ability to effectively minimize the size of hydrate agglomerate particles and then disperse those particles into the hydrocarbon phase. Chemical performance was evaluated by determining the maximum treatable water cut (water to oil ratio) and the minimum chemical dosage to register a pass in the rocking cell test.

The rocking cell had two parts, a manifold and a cell body. The manifold was made of stainless steel fittings welded together and had three stems. Inlet stem was used to charge gas into the cell. Outlet stem was used to release the gas out of cell. Third stem was connected to a transducer, which measured the pressure inside of the cell. The cell body had three layers. The outer layer was a polycarbonate tube, the thickness of which was 0.7 cm. The middle layer was made of stainless steel and was connected to the manifold. The inner layer was high-pressure sapphire tube with an outer diameter of 2.8 cm, inner diameter of 1.85 cm, and length of 5 cm. This sapphire tube was rated up 3,000 psi. A stainless steel ball of 1.6 cm of diameter was located inside the sapphire tube to induce turbulence and mix fluids during the rocking process.

Test fluids contained three components. For this anti-agglomerate test, a correct amount of warm Magnolia crude oil was injected into the cell. Next, a solution of 7% by weight of NaCl and DI water was injected with the accurate amount according to the percent of aqueous phase. The tested anti-agglomerate of the invention was the final component injected into the cell. The dosage of chemical was based on the volume of aqueous phase. Test was set at 21° C. as initial condition. Each cell was charged by Green Canyon gas and pressurized up to 2,100 psi. All cells were rocked for at least 1.5 to 2 hours until fluid was saturated and pressure stabilized. The temperature was reduced to a set point of 4° C. The cells were rocked for 16 hours, held static for 6 hours, and rocked back for 2 hours. Pressure data was recorded during this time. Observations were taken every two to three hours, before rocking was stopped and also immediately after the restart. The comparative examples are described in U.S. patent application Ser. No. 12/396,076, "Compositions Containing Amide Surfactants and Methods for Inhibiting the Formation of Hydrate Agglomerates," filed Mar. 2, 2009, currently pending. Results are shown in Table 2.

TABLE 2

| Structure | Maximum Water Cut |
|---|---|
| Blank | None |
| Comparative Example A | 50% |
| Comparative Example B | 50% |
| 1 | 55% |
| 4 | 55% |
| 7 | 55% |
| 10 | 55% |
| 13 | 60% |
| 16 | 60% |

It can be seen in Table 2, that the compositions of the invention provide not only an increase in chemical performance in the rocking cell test, but a significant increase in overboard water quality. The compositions of the invention (which are surfactants) have a tendency to stabilize the emulsion at the oil/water interface. These compositions have also been shown in laboratory bottle test experiments to result in enhanced water quality and rapid destabilization of emulsions in comparison to Comparative Examples A and B (Table 2).

All of the compositions and methods disclosed and claimed herein can be made and executed without undue experimentation in light of the present disclosure. While this invention may be embodied in many different forms, there are described in detail herein specific preferred embodiments of the invention. The present disclosure is an exemplification of the principles of the invention and is not intended to limit the invention to the particular embodiments illustrated. In addition, unless expressly stated to the contrary, use of the term "a" is intended to include "at least one" or "one or more." For example, "a device" is intended to include "at least one device" or "one or more devices."

Any ranges given either in absolute terms or in approximate terms are intended to encompass both, and any definitions used herein are intended to be clarifying and not limiting. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges (including all fractional and whole values) subsumed therein.

Furthermore, the invention encompasses any and all possible combinations of some or all of the various embodiments described herein. Any and all patents, patent applications, scientific papers, and other references cited in this application, as well as any references cited therein, are hereby incorporated by reference in their entirety. It should also be understood that various changes and modifications to the presently preferred embodiments described herein will be apparent to those skilled in the art. Such changes and modifications can be made without departing from the spirit and scope of the invention and without diminishing its intended advantages. It is therefore intended that such changes and modifications be covered by the appended claims.

The claimed invention is:

1. A composition comprising the following formula and optionally salts thereof:

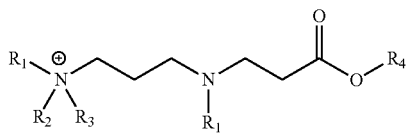

wherein each $R_1$ is independently $C_1$-$C_{10}$ alkyl, benzyl, or H;
wherein $R_2$ is $C_1$-$C_{10}$ alkyl;
wherein $R_3$ $C_1$-$C_{10}$ alkyl; and
wherein $R_4$ is $C_4$-$C_{22}$ alkyl or alkenyl.

2. The composition of claim 1, wherein each alkyl is independently selected from the group consisting of: a straight chain alkyl, a branched chain alkyl, a cyclic alkyl, a saturated version of the foregoing, an unsaturated version of the foregoing, and combinations thereof.

3. The composition of claim 1, wherein the alkyl for each of $R_1$, $R_2$, and $R_3$ is independently selected from the group consisting of: methyl; ethyl; propyl; butyl; pentyl; hexyl; heptyl; octyl; nonyl; decyl; and combinations thereof.

4. The composition of claim 1, wherein the alkyl for R4 is selected from the group consisting of: butyl; pentyl; hexyl; heptyl; octyl; nonyl; decyl; and combinations thereof.

5. The composition of claim 1, wherein $R_2$ and $R_3$ are methyl.

6. The composition of claim 1, wherein $R_2$ and $R_3$ are butyl or n-butyl.

7. The composition of claim 1, further comprising counterion X— as shown in the general formula below

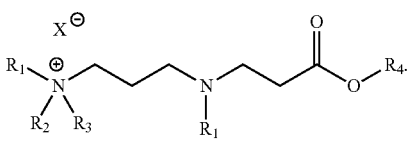

8. The composition of claim 7, wherein the counterion is a halide.

9. The composition of claim 8, wherein the halide is selected from the group consisting of: fluoride, chloride, bromide, iodide, and any combination thereof.

10. The composition of claim 7, wherein the counterion is a carboxylate selected from: reaction with mineral acid; acrylic acid; acetic acid; methacrylic acid; glycolic acid; thioglycolic acid; propionic acid; butyric acid; and combinations thereof.

11. The composition of claim 1, further comprising at least one component selected from the group consisting of: thermodynamic hydrate inhibitors, one or more kinetic hydrate inhibitors, one or more additional anti-agglomerants, and combinations thereof.

12. The composition of claim 1, further comprising at least one component selected from the group consisting of: asphaltene inhibitors, paraffin inhibitors, corrosion inhibitors, scale inhibitors, emulsifiers, water clarifiers, dispersants, emulsion breakers, and combinations thereof.

13. The composition of claim 1, further comprising at least one polar or nonpolar solvent or a mixture thereof.

14. The composition of claim 1, further comprising at least one solvent selected from the group consisting of isopropanol, methanol, ethanol, 2-ethylhexanol, heavy aromatic naptha, toluene, ethylene glycol, ethylene glycol monobutyl ether (EGMBE), diethylene glycol monoethyl ether, xylene, and combinations thereof.

15. A method of inhibiting the formation of hydrate agglomerates in a fluid comprising water, gas, and optionally liquid hydrocarbon comprising adding to the fluid an effective anti-agglomerant amount of the composition of claim 1.

16. The method of claim 15, wherein said fluid has a salinity of 1% to 25% w/w percent total dissolved solids.

17. The method of claim 15, wherein said fluid has a water cut from 1 to 80% v/v total dissolved solids.

18. The method of claim 15, wherein the fluid is contained in an oil or gas pipeline or refinery.

19. A composition comprising at least one or any combination of the formulas and optionally salts thereof:

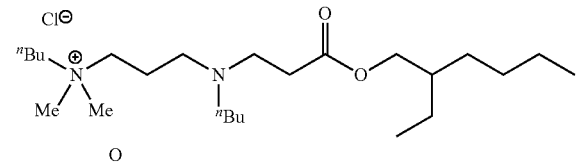

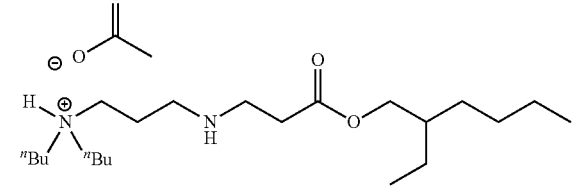

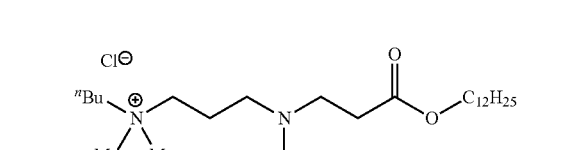

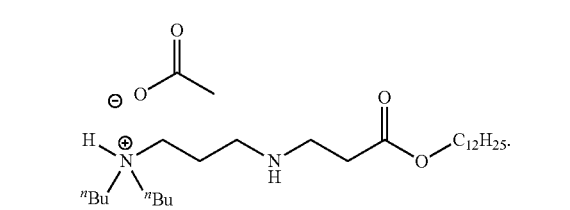

20. The composition of claim 1, comprising at least one or any combination of the following formulas:
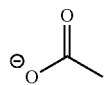
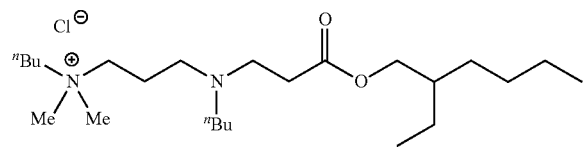
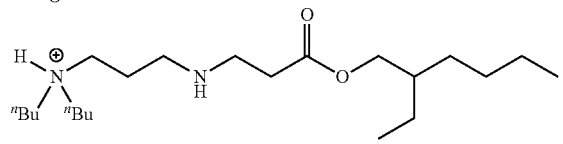
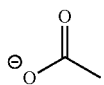
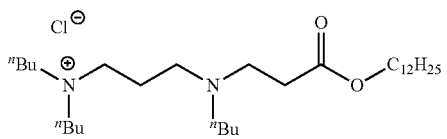
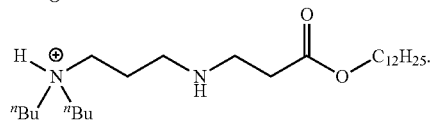
* * * * *